(12) United States Patent
Burgi et al.

(10) Patent No.: US 8,277,457 B1
(45) Date of Patent: Oct. 2, 2012

(54) ORTHOPAEDIC INSERTER USING A COLLET MECHANISM

(75) Inventors: Jonas Burgi, Moutier (CH); Yves Desarzens, Corgemont (CH); Andre Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 266 days.

(21) Appl. No.: 12/724,505

(22) Filed: Mar. 16, 2010

Related U.S. Application Data

(63) Continuation-in-part of application No. 11/201,270, filed on Aug. 10, 2005, now Pat. No. 7,682,363.

(60) Provisional application No. 60/634,467, filed on Dec. 9, 2004.

(51) Int. Cl.
*A61B 17/58* (2006.01)

(52) U.S. Cl. ............................................. 606/91; 606/81

(58) Field of Classification Search .................... 606/80, 606/81, 91, 99, 79, 86 R
See application file for complete search history.

(56) References Cited

U.S. PATENT DOCUMENTS

| | | | |
|---|---|---|---|
| 1,942,422 A | 1/1934 | Hanna | |
| 4,305,394 A | 12/1981 | Bertuch | |
| D272,648 S | 2/1984 | Bolesky et al. | |
| D273,806 S | 5/1984 | Bolesky et al. | |
| 4,475,549 A | 10/1984 | Oh | |
| 4,520,511 A | 6/1985 | Gianezio et al. | |
| 4,528,980 A | 7/1985 | Kenna | |
| 4,587,964 A | 5/1986 | Walker et al. | |
| 4,632,111 A | 12/1986 | Roche | |
| 4,716,894 A | 1/1988 | Lazzeri et al. | |
| 4,765,328 A | 8/1988 | Keller et al. | |
| 4,904,267 A | 2/1990 | Bruce et al. | |
| 4,919,679 A | 4/1990 | Averill et al. | |
| 4,921,493 A | 5/1990 | Webb, Jr. et al. | |
| 5,019,105 A | 5/1991 | Wiley | |
| 5,037,424 A | 8/1991 | Aboczsky | |
| 5,061,270 A | 10/1991 | Aboczky | |
| 5,062,854 A | 11/1991 | Noble et al. | |
| 5,089,003 A | 2/1992 | Fallin et al. | |
| 5,116,339 A | 5/1992 | Glock | |
| 5,124,106 A | 6/1992 | Morr et al. | |
| 5,133,766 A | 7/1992 | Halpern | |
| 5,169,399 A | 12/1992 | Ryland et al. | |
| 5,190,549 A | 3/1993 | Miller et al. | |
| 5,201,779 A * | 4/1993 | Shiao | 606/91 |
| 5,234,432 A | 8/1993 | Brown | |
| 5,261,915 A | 11/1993 | Durlacher et al. | |
| 5,324,293 A | 6/1994 | Rehman | |

(Continued)

FOREIGN PATENT DOCUMENTS

EP 0453694 10/1991

(Continued)

OTHER PUBLICATIONS

Smith & Nephew Polarcup Dual Mobility System.

(Continued)

*Primary Examiner* — Jan Christopher Merene
(74) *Attorney, Agent, or Firm* — Michael F. Scalise

(57) ABSTRACT

An orthopedic prosthetic inserter used for the implantation of an acetabular prosthetic cup implant. The inserter consists of a drive train, a C-shaped housing, and a collet mechanism used to attach a prosthetic cup implant. When activated by the drive train, the collet mechanism expands to draw the prosthesis towards the collet mechanism and create a substantially friction tight engagement therebetween.

20 Claims, 20 Drawing Sheets

U.S. PATENT DOCUMENTS

| | | | |
|---|---|---|---|
| 5,342,362 A | 8/1994 | Kenyon et al. | |
| 5,364,403 A | 11/1994 | Petersen et al. | |
| 5,417,696 A | 5/1995 | Kashuba et al. | |
| 5,443,471 A | 8/1995 | Swaiger | |
| 5,485,887 A | 1/1996 | Mandanis | |
| 5,540,697 A | 7/1996 | Rehmann et al. | |
| 5,584,837 A | 12/1996 | Petersen et al. | |
| 5,649,931 A * | 7/1997 | Bryant et al. | 606/104 |
| 5,658,294 A | 8/1997 | Sederholm | |
| 5,665,091 A | 9/1997 | Nobel et al. | |
| 5,683,399 A | 11/1997 | Jones | |
| 5,707,374 A | 1/1998 | Schmidt | |
| 5,720,750 A | 2/1998 | Koller et al. | |
| 5,863,295 A | 1/1999 | Averill et al. | |
| 5,913,860 A | 6/1999 | Scholl | |
| 5,976,148 A | 11/1999 | Charpenet et al. | |
| 5,993,455 A | 11/1999 | Noble | |
| 6,063,124 A | 5/2000 | Amstutz | |
| 6,120,508 A | 9/2000 | Grunig et al. | |
| 6,197,065 B1 | 3/2001 | Martin et al. | |
| 6,432,141 B1 | 8/2002 | Stocks et al. | |
| 6,451,058 B2 | 9/2002 | Tuke et al. | |
| 6,626,913 B1 | 9/2003 | McKinnon et al. | |
| 6,663,636 B1 | 12/2003 | Lin | |
| 6,811,569 B1 | 11/2004 | Afriat et al. | |
| 7,192,449 B1 | 3/2007 | McQueen et al. | |
| 7,335,207 B1 | 2/2008 | Smith | |
| 7,341,593 B2 | 3/2008 | Auxepaules et al. | |
| 7,396,357 B2 | 7/2008 | Tornier et al. | |
| 7,585,301 B2 | 9/2009 | Santarella et al. | |
| 7,591,821 B2 | 9/2009 | Kelman | |
| 7,604,667 B2 | 10/2009 | DeSmet et al. | |
| 7,621,921 B2 | 11/2009 | Parker | |
| 7,922,726 B2 | 4/2011 | White | |
| 2001/0051830 A1 | 12/2001 | Tuke et al. | |
| 2002/0004660 A1 | 1/2002 | Henniges et al. | |
| 2002/0116007 A1 | 8/2002 | Lewis | |
| 2002/0177854 A1 | 11/2002 | Tuke et al. | |
| 2002/0193797 A1 | 12/2002 | Johnson et al. | |
| 2003/0009234 A1 | 1/2003 | Treacy et al. | |
| 2003/0050645 A1 | 3/2003 | Parker et al. | |
| 2003/0083668 A1 | 5/2003 | Rogers et al. | |
| 2003/0088316 A1 | 5/2003 | Ganjianpour | |
| 2003/0187512 A1 | 10/2003 | Frederick et al. | |
| 2003/0220698 A1 | 11/2003 | Mears et al. | |
| 2003/0229356 A1 | 12/2003 | Dye | |
| 2004/0034367 A1 * | 2/2004 | Malinowski | 606/129 |
| 2004/0215198 A1 * | 10/2004 | Marnay et al. | 606/86 |
| 2004/0215200 A1 | 10/2004 | Tornier et al. | |
| 2005/0038443 A1 | 2/2005 | Hedley et al. | |
| 2005/0075736 A1 | 4/2005 | Collazo | |
| 2005/0137603 A1 | 6/2005 | Belew et al. | |
| 2005/0171548 A1 | 8/2005 | Kelman | |
| 2005/0187562 A1 | 8/2005 | Grimm et al. | |
| 2005/0222572 A1 | 10/2005 | Chana | |
| 2005/0228395 A1 | 10/2005 | Auxepaules et al. | |
| 2005/0234462 A1 | 10/2005 | Hershberger | |
| 2005/0246031 A1 | 11/2005 | Frederick et al. | |
| 2006/0052780 A1 | 3/2006 | Errico et al. | |
| 2006/0149285 A1 | 7/2006 | Burgi et al. | |
| 2007/0156155 A1 | 7/2007 | Parker | |
| 2007/0167952 A1 | 7/2007 | Burgi et al. | |
| 2007/0173856 A1 * | 7/2007 | Parker | 606/99 |
| 2007/0225725 A1 | 9/2007 | Heavener et al. | |
| 2007/0270783 A1 | 11/2007 | Zumsteg et al. | |
| 2007/0288096 A1 | 12/2007 | Surma | |
| 2007/0293869 A1 | 12/2007 | Conte et al. | |
| 2008/0004628 A1 | 1/2008 | White | |
| 2008/0021481 A1 | 1/2008 | Burgi | |
| 2008/0033444 A1 | 2/2008 | Bastian et al. | |
| 2008/0077249 A1 | 3/2008 | Gradel | |
| 2008/0146969 A1 | 6/2008 | Kurtz | |
| 2008/0154261 A1 | 6/2008 | Burgi | |
| 2008/0243127 A1 | 10/2008 | Lang et al. | |
| 2008/0255565 A1 | 10/2008 | Fletcher | |
| 2008/0255568 A1 | 10/2008 | Tornier et al. | |
| 2008/0262503 A1 | 10/2008 | Muller | |
| 2008/0275450 A1 | 11/2008 | Myers et al. | |
| 2009/0112214 A1 | 4/2009 | Philippon et al. | |
| 2009/0182334 A1 | 7/2009 | Brehm | |
| 2009/0192515 A1 | 7/2009 | Lechot et al. | |
| 2009/0240256 A1 | 9/2009 | Smith | |
| 2009/0281545 A1 | 11/2009 | Stubbs | |

FOREIGN PATENT DOCUMENTS

| | | |
|---|---|---|
| EP | 0470912 | 2/1992 |
| EP | 0535973 | 4/1993 |
| EP | 357302 | 7/1994 |
| EP | 638299 | 2/1995 |
| EP | 1308140 | 5/2003 |
| EP | 1190687 | 7/2004 |
| EP | 1438936 | 7/2004 |
| EP | 1447058 | 8/2004 |
| WO | 9511641 | 5/1995 |
| WO | 0012832 | 3/2000 |
| WO | 0106964 | 2/2001 |
| WO | 2005044153 | 5/2005 |
| WO | 2006061708 | 6/2006 |
| WO | 2007098549 | 9/2007 |
| WO | 2008128282 | 10/2008 |
| WO | 2009136284 | 11/2009 |

OTHER PUBLICATIONS

European Search Report dated Apr. 15, 2011.

* cited by examiner

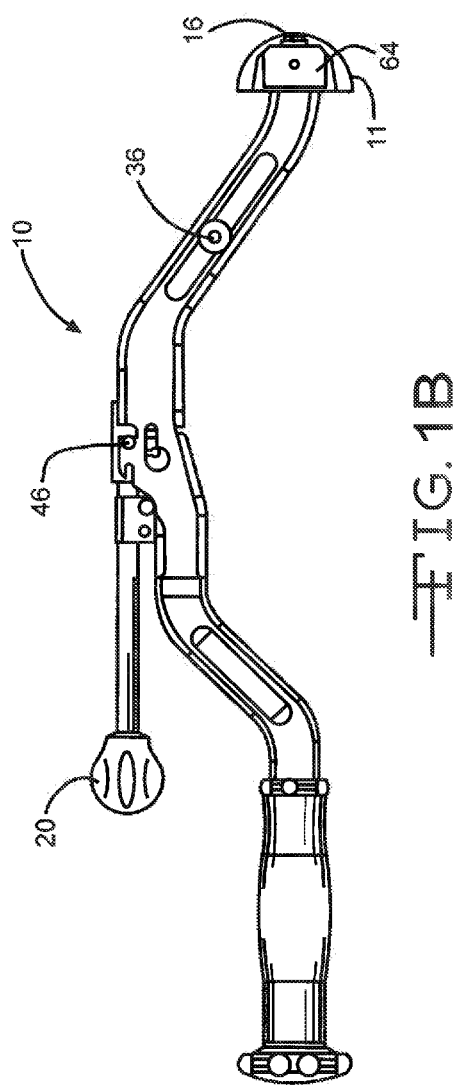

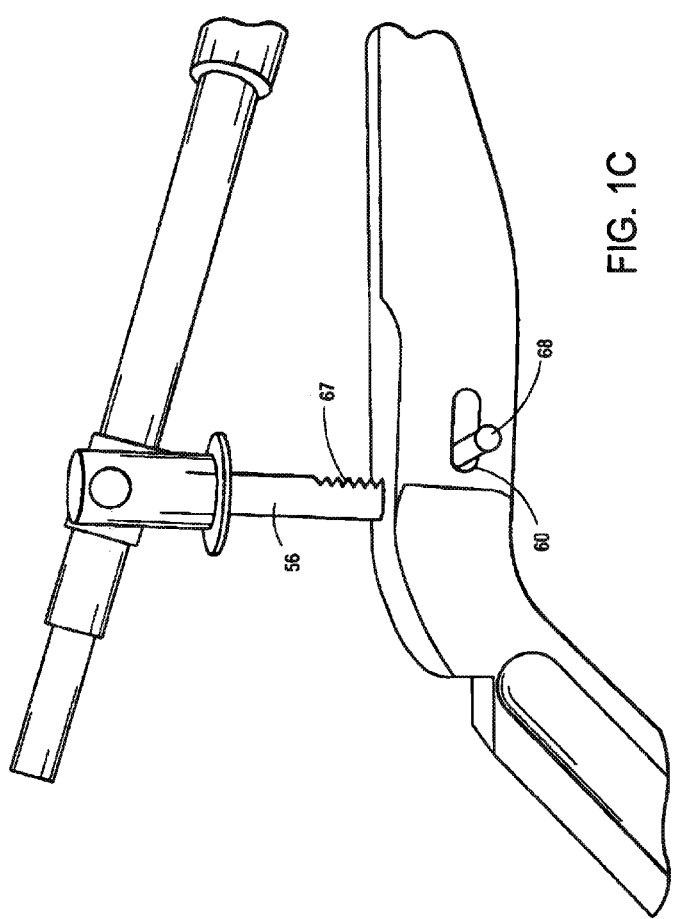

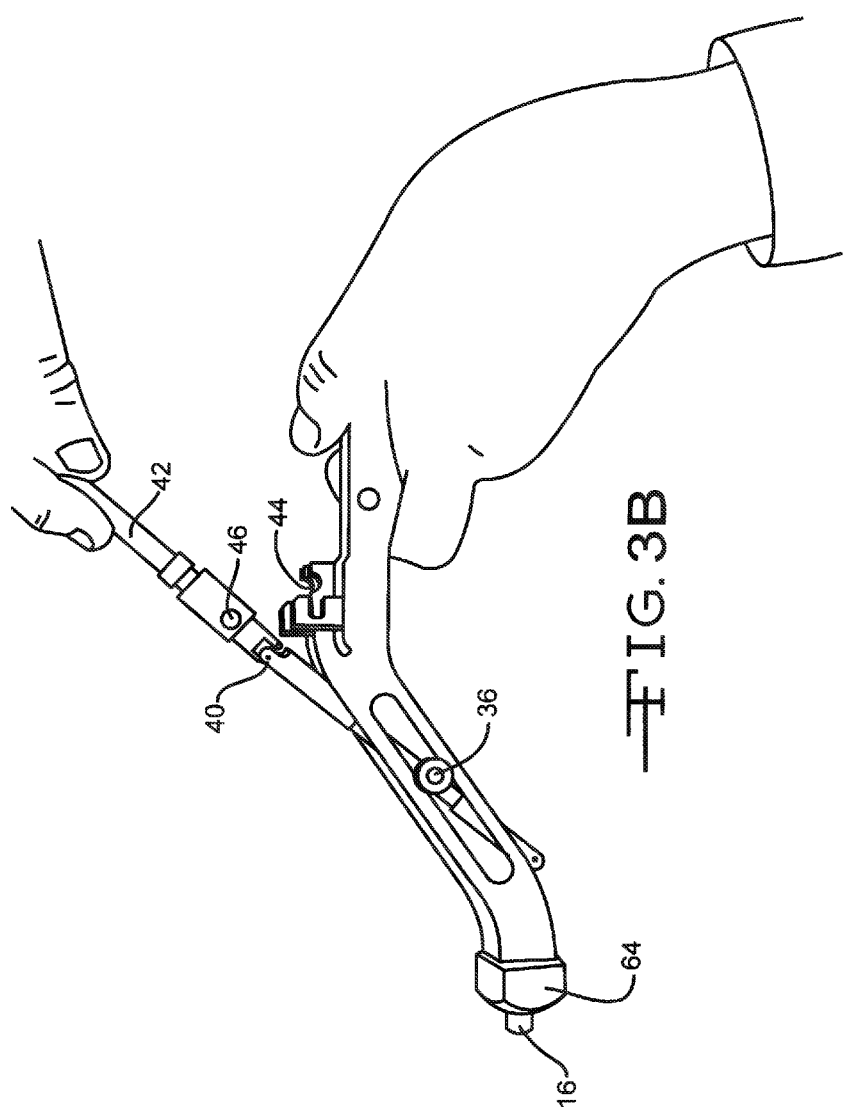

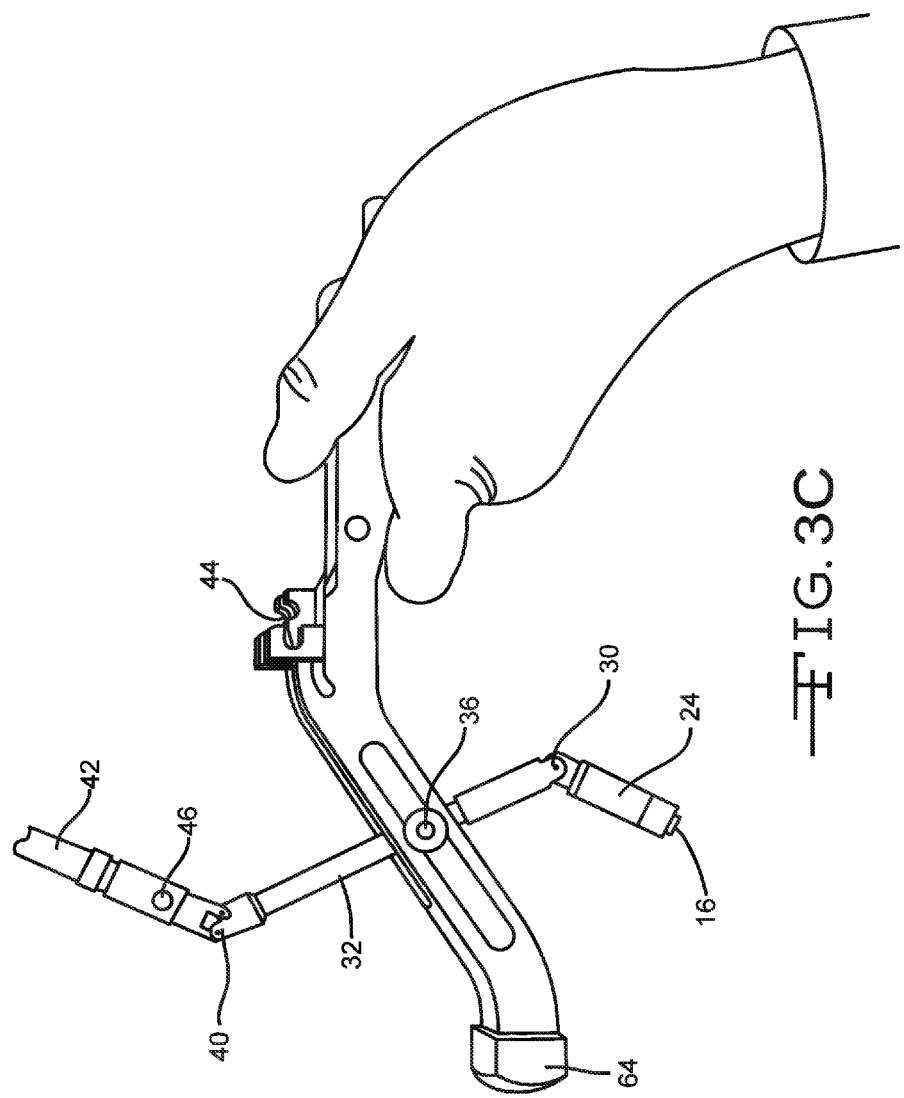

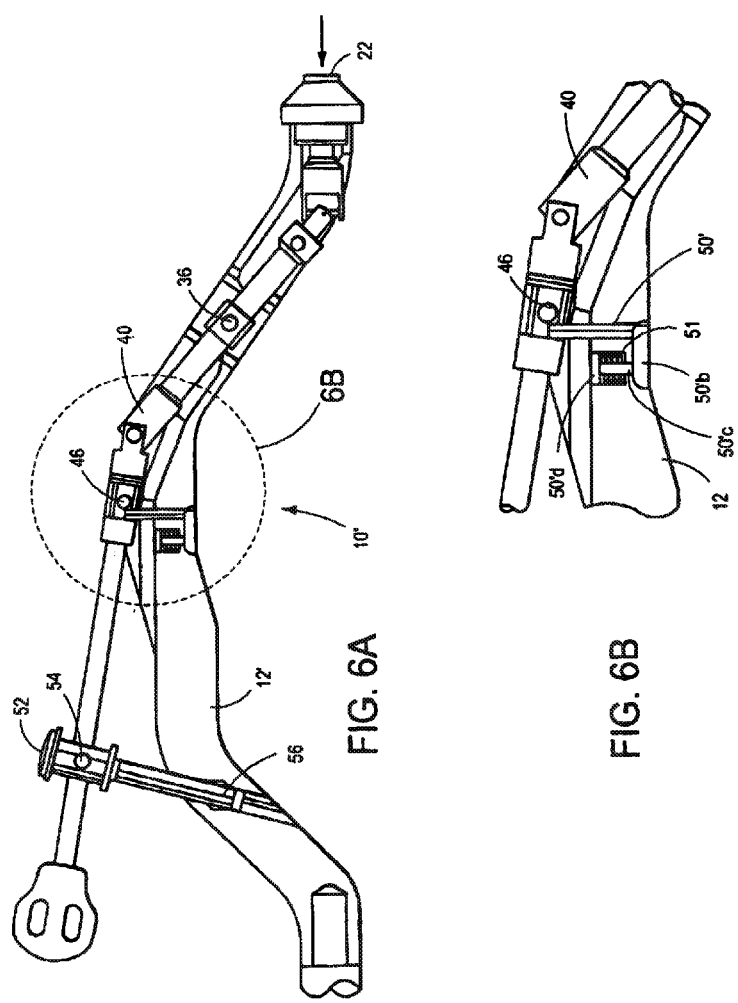

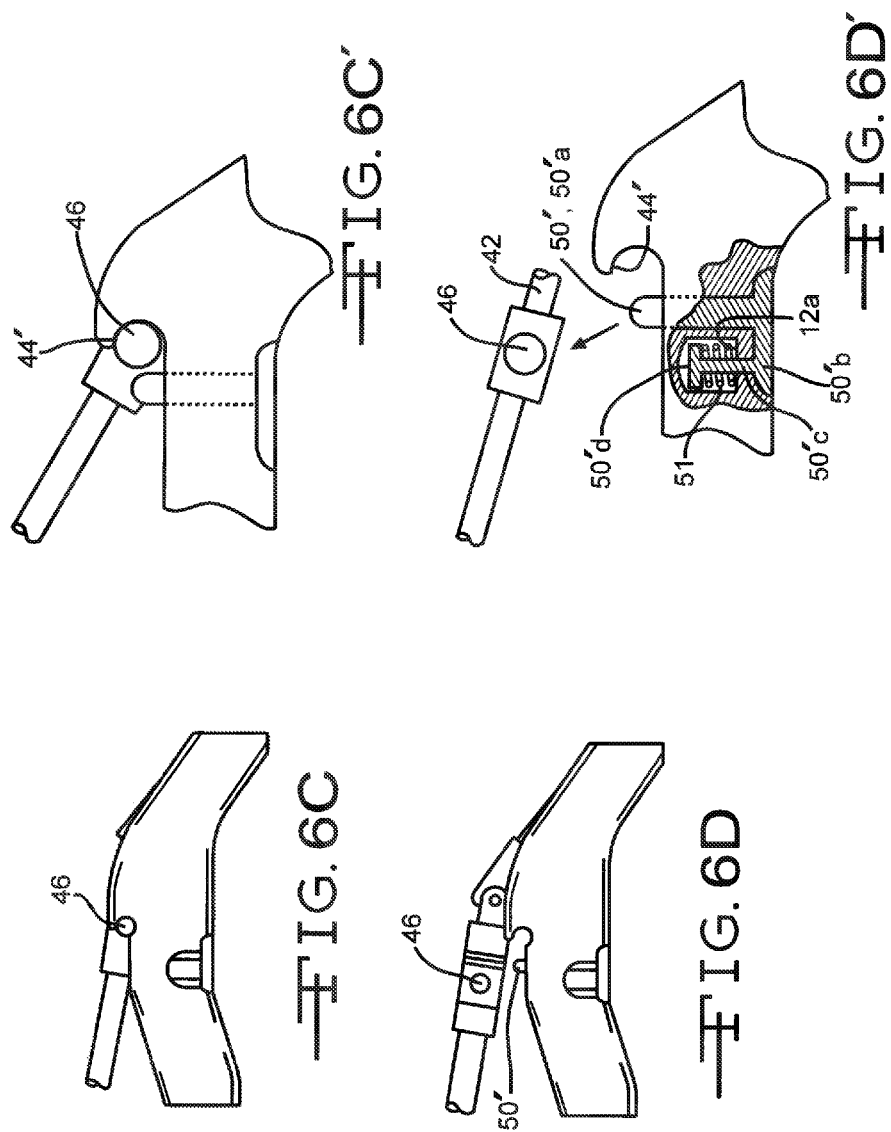

US 8,277,457 B1

ORTHOPAEDIC INSERTER USING A COLLET MECHANISM

CROSS REFERENCE TO RELATED APPLICATIONS

This application is a continuation in part of U.S. application Ser. No. 11/201,270, filed on Aug. 10, 2005, now U.S. Pat. No. 7,682,363 to Burgi et al., which claims priority to U.S. Provisional Application Ser. No. 60/634,467, filed Dec. 9, 2004.

BACKGROUND OF THE INVENTION

This invention relates to surgical inserters for aiding in installing orthopedic prostheses, and, more particularly, to easily sterilizable inserters for installing acetabular implants in the acetabular socket.

Complicated mechanical devices have crevices and recesses that are difficult, if not almost impossible to clean with ease. Devices that are not properly cleaned and sterilized run the risk of disease transfer from patient to patient following the emergence of certain "prions" that are not killed by normal hospital sterilization and need to be physically removed by washing/rinsing.

Further, in surgical procedures in which access to the treatment site is limited, it is difficult to use current solutions without subjecting the patient to repeated abrasion and tissue trauma when inserting and extracting surgical instruments.

Further, the insertion of the implant is often problematic, and the orientation of the implant, particularly any fixing holes that might be pre-drilled in the implant is often critical to minimize recovery time of the patient. Still further, once the appropriate position of the implant is selected, it is often difficult to ensure that the position does not change upon insertion of the assembly through the incision.

What is needed therefore is an inserter that is easy to adjust, disassemble, and clean. Further, what is needed is an inserter that enables the surgeon to better maneuver, position and install an implant in a particular angular orientation.

SUMMARY OF THE INVENTION

An acetabular inserter aids a surgeon in controlling the installation of an acetabular cup prosthesis generally having a central, female aperture. The inserter has a housing which encloses a drive train having, at a far end, a prosthesis engaging interface, and at the opposite end, a handle which facilitates turning of the drive train by the operator. The inserter enables easy orientation of a prosthesis attached to its end, which is important because the prosthesis often has pre-drilled holes and thus, these must be properly positioned prior to fastening through these holes.

An objective of the invention is to be "easily cleaned" by quick and modular disassembly which enables access to all surfaces that they can be cleaned, the reduction in number of small radius internal corners, crevices and small gaps and the absence of blind holes.

Another object of the invention is to provide an inserter which enables the implant to be locked in an angular orientation prior to installation of the implant.

Another object of the invention is to provide a dual mechanism that uses common components to lock the implant in place as well as to provide for easy disassembly for cleaning and sterilization.

Another object of the invention is to minimize the number of pieces and the risk that parts could be lost.

BRIEF DESCRIPTION OF THE DRAWINGS

The attached drawings represent, by way of example, different embodiments of the subject of the invention.

FIG. 1B is a side view of the inserter of the invention.

FIG. 1C is a perspective view of the inserter of the invention showing a one-way catch mechanism.

FIG. 3B is a perspective view of the inserter of the invention, showing another step of disassembly for cleaning.

FIG. 3C is a perspective view of the inserter of the invention, showing a stage of disassembly for cleaning.

FIG. 6A is a side, cross sectional view of an alternate embodiment of the inserter of the invention having a drive train locking device.

FIG. 6B is a detail view of the portion 6B of the drive train locking device shown in FIG. 6A.

FIGS. 6C-6D are partial side views of the inserter of FIG. 6A showing the removal of the driver train from within the housing of the inserter.

FIG. 12B is the sectional view of FIG. 12A wherein the mechanism is shown in an unlocked position.

DETAILED DESCRIPTION OF THE PREFERRED EMBODIMENT(S)

Figure 1A:
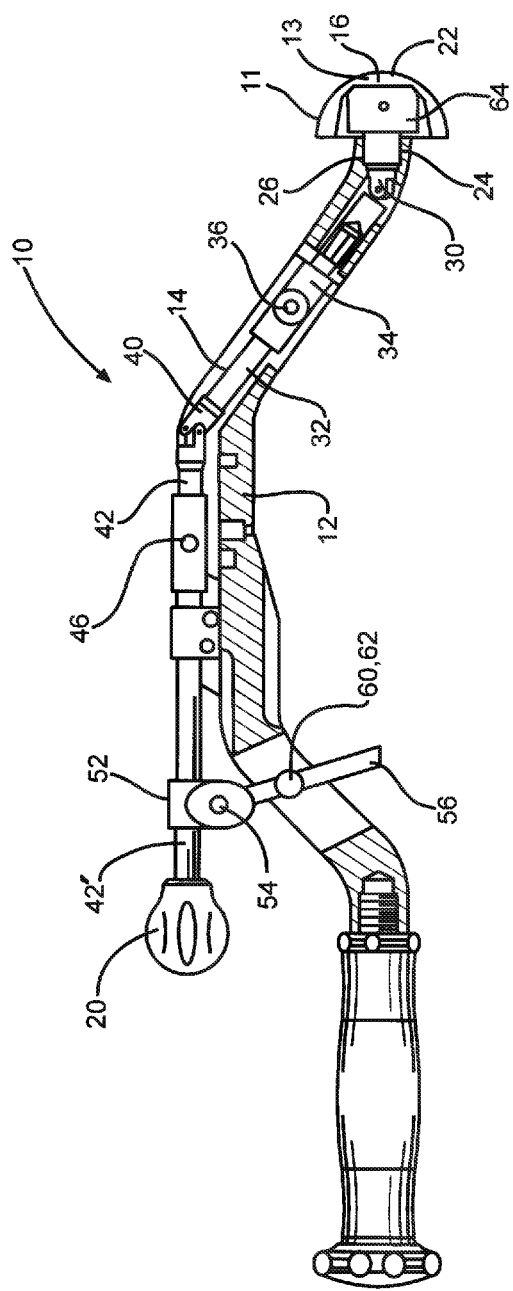
FIG. 1A is a cross-sectional side view of the inserter of the invention.

Referring now to FIGS. 1A-1C, an acetabular inserter 10 is provided to aid the surgeon in controlling the installation of an acetabular cup prosthesis 11 having a central, female aperture 13. The inserter 10 has a housing 12 which encloses a drive train 14 having, at a far end, a prosthesis engaging interface 16 (preferably threaded), and at the opposite end, a handle 20 which facilitates turning of the drive train by the operator. The housing 12 may be C-shaped, as shown, in order to minimize the invasiveness of the surgery by better clearing anatomical structures and tissue.

The interface 16 is cut on a boss 22 on a cylindrical piston 24 which slides in an axial hole 26 in the housing 12. The interface 16 is preferably threaded. The piston 24 is connected by way of a first U-joint 30 to a lever 32 which slides in a pivoting sleeve 34 fixed to the housing 12 via a pivot 36. The lever 32 is connected via a second U-joint 40 to a second pivoting lever 42 which is fixed to pivot in a catch 44 on a pivot pin 46. The catch 44 is essentially a divot or a seat cut into the housing 12, against which the pivot pin 46 of the lever 42 is captured when a slide 50 is slide over the pin when engaged against the seat.

A slideable sleeve 52 slides over the lever 42 and has a trunnion 54 to which a rod 56 is pivotally attached. The rod 56 passes through a one-way catch 60 in the housing 12. The one-way catch 60 can be a captured split wedge sleeve 62 having an inner diameter that just matches the outer diameter of the rod 56 and which is captured in a recess having a matching conical surface that surrounds the sleeve so as to allow the rod 56 to slide into the housing 12, but to prevent the rod from sliding out of the housing unless an unlock lever (not shown) is activated, such lever merely lifting the sleeve 62 out of engagement with the conical surface so as not to lock and to permit the rod to back out of the housing. Any number of alternative one-way lock devices may be used, however, the selection of which being within the skill of a person of ordinary skill in this field.

Referring now to FIG. 1C, an alternative embodiment of the one-way catch mechanism 60 is shown. In this embodiment, the rod 56 passes through a one-way catch 60 in the housing 12. The one-way catch 60 has an inner recess that matches the outer diameter of the rod 56. The inner recess has a ratchet pawl (not shown) that locks against the one-way ratchet teeth 67 so as to allow the rod 56 to slide into the housing 12, but to prevent the rod from sliding out of the housing unless an unlock lever 68 is activated, such lever merely pulling the pawl away from the teeth to permit the rod to back out of the housing.

A polymeric impactor head 64 is molded over the end of the housing 12, to absorb the impact stresses incurred during use as an impactor. The head 64 is selected so as to have good frictional characteristics as well. Nevertheless, a metal, non-molded head may also be used with satisfactory results.

Figure 2A:
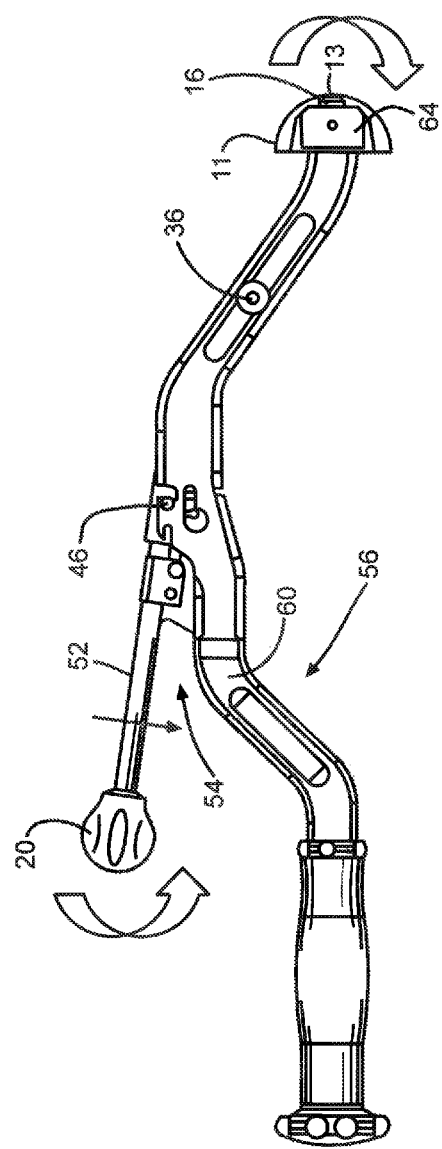
FIG. 2A is an operational side view of the inserter of the invention.
Figure 2B:
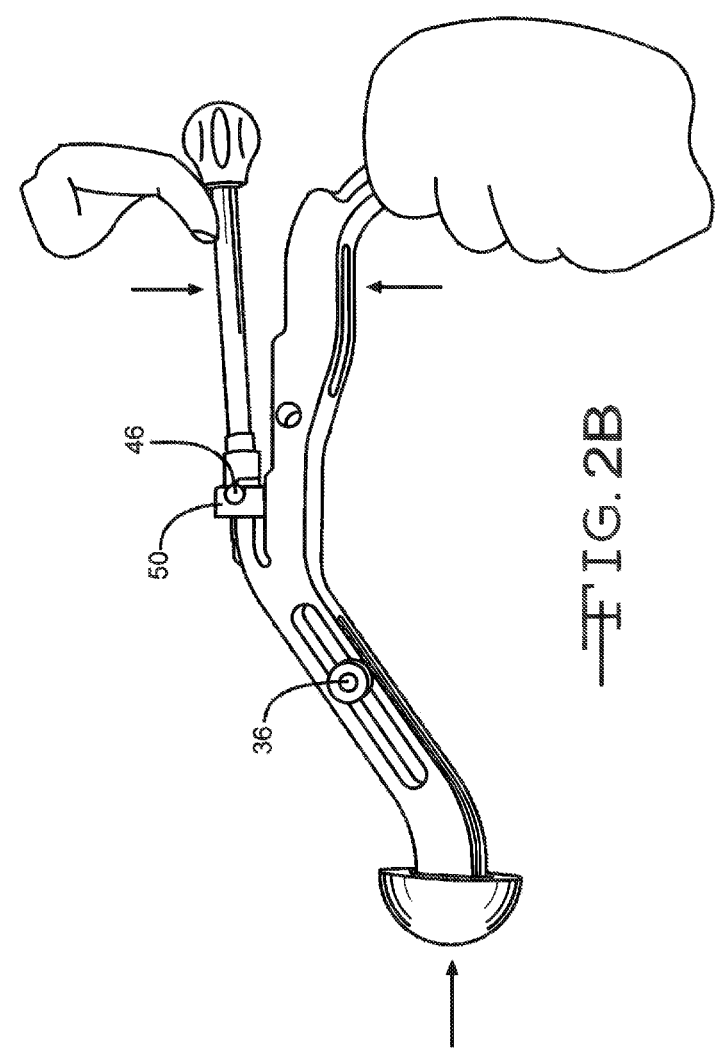
FIG. 2B is an operational back view of the inserter of the invention.
Figure 3A:
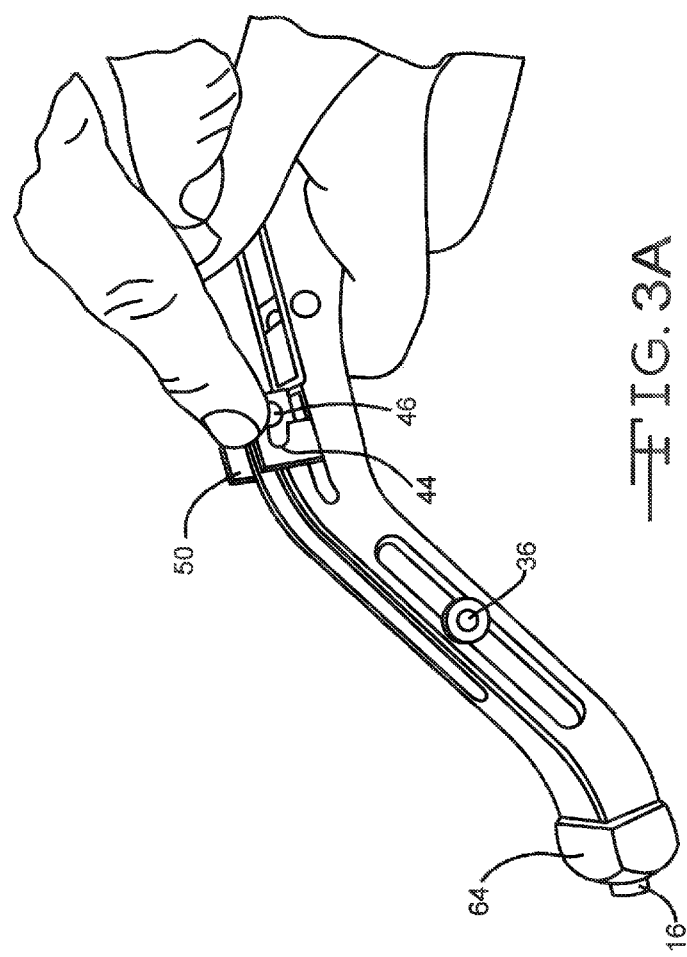
FIG. 3A is a perspective view of the inserter of the invention, showing a step of disassembly for cleaning.
Figure 3D:
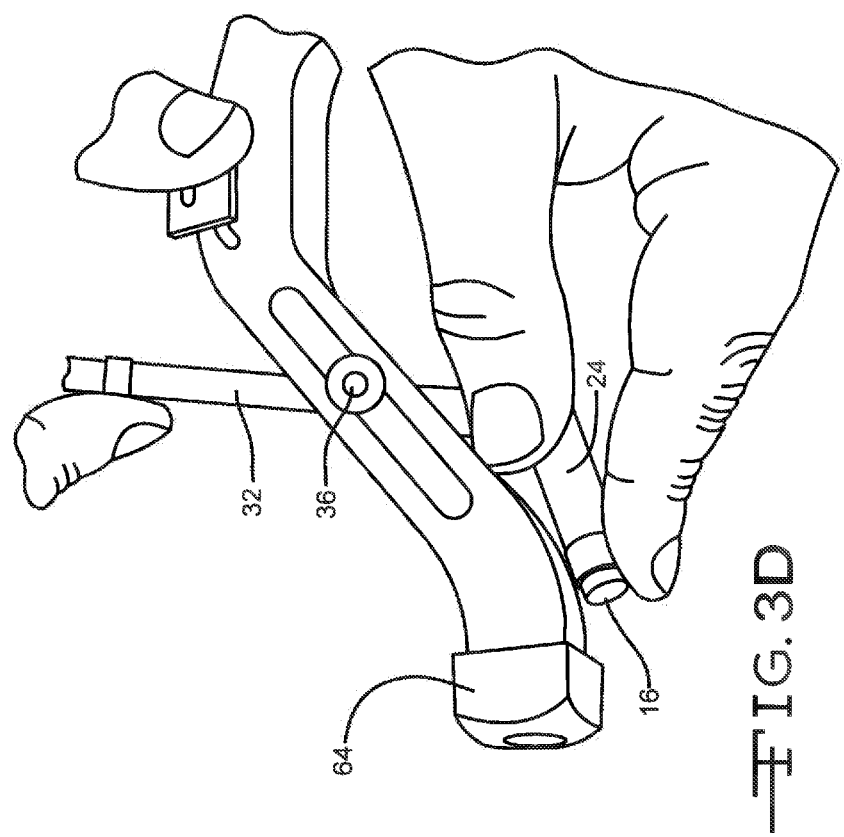
FIG. 3D is a perspective view of the inserter of the invention, showing a stage of re-assembly after cleaning.

Referring now to FIGS. 2A-2B, in operation, the interface 16 (preferably threaded) of the piston 24 is engaged with the hole 13 of the prosthesis 11. The operator may rotate the handle 20 about its axis to turn the drive train 14 in order to interface the piston 24 into the hole 13 or to orient the prosthesis in what he believes to be a correct or an initial position. Then, an end 42' of the lever 42 is urged downwardly toward the housing 12. Such downward movement acts through the drive train 14 to draw the piston 24 into the housing 12, and thus to cause the inner surface of the prosthesis 11 to be drawn against the head 64 so as to create a normal force between the inside of the prosthesis 11 and the head 64 so as to prevent rotation of the prosthesis 11 relative to the housing 12. The operator may use the one-way locking mechanism 62 to lock the lever 42 in a position so as to lock the prosthesis 11 against the head 64, thus enabling the surgeon to pre-set and lock the position of the prosthesis prior to the installation thereof. Note that orientation of the prosthesis 11 is important because the prosthesis 11 often has pre-drilled holes 4 (shown in FIG. 8) and thus, these must be properly positioned prior to fastening through these holes.

The "easily cleaned" objective of the invention enables access to all surfaces that they can be cleaned (parts covering another part can be moved or removed to expose all surfaces), the reduction in number of small radius internal corners, crevices and small gaps and the absence of blind holes.

Referring now to FIGS. 3A-3D, in the embodiment shown, the device 10 is disassembled for cleaning by simply sliding the slide 50 back so as to release the pivot 46 and then lift the drive train 14 out of the housing 12 but allow it to remain pivotally connected at pivot 36. As the drive train 14 is pivoted, the piston 24 is drawn out of the hole 26 in the housing 12. To reassemble after cleaning, the piston 24 is reinserted into the hole 26 and the drive train 14 is rotated back into position, with the one-way locking mechanism entering its receiver and the pivot 46 again entering into the catch 44. The slide 50 is then slid over the pivot 46 and the inserter 10 is again ready for use.

Figure 4:
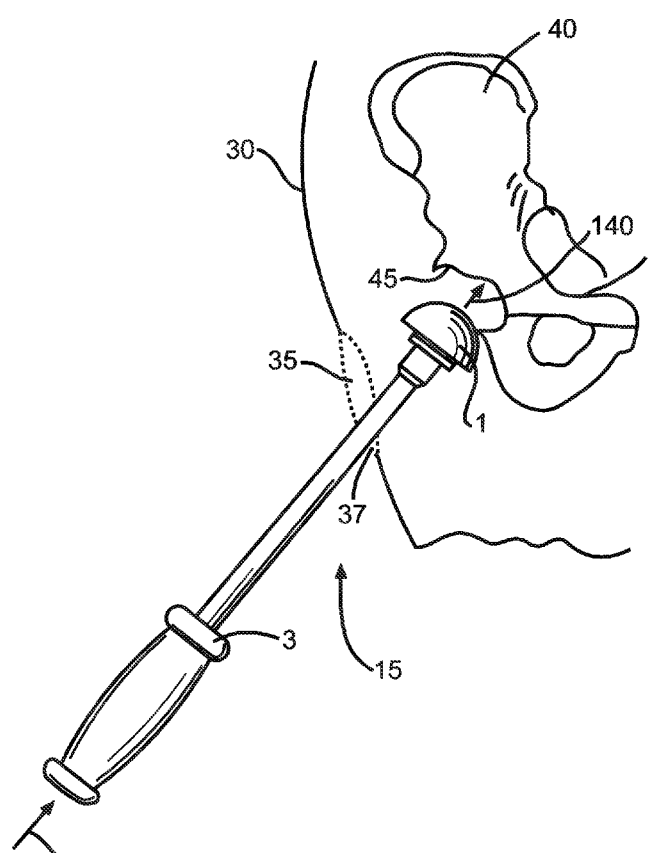
FIG. 4 is a schematic view of a prior art inserter.
Figure 5:
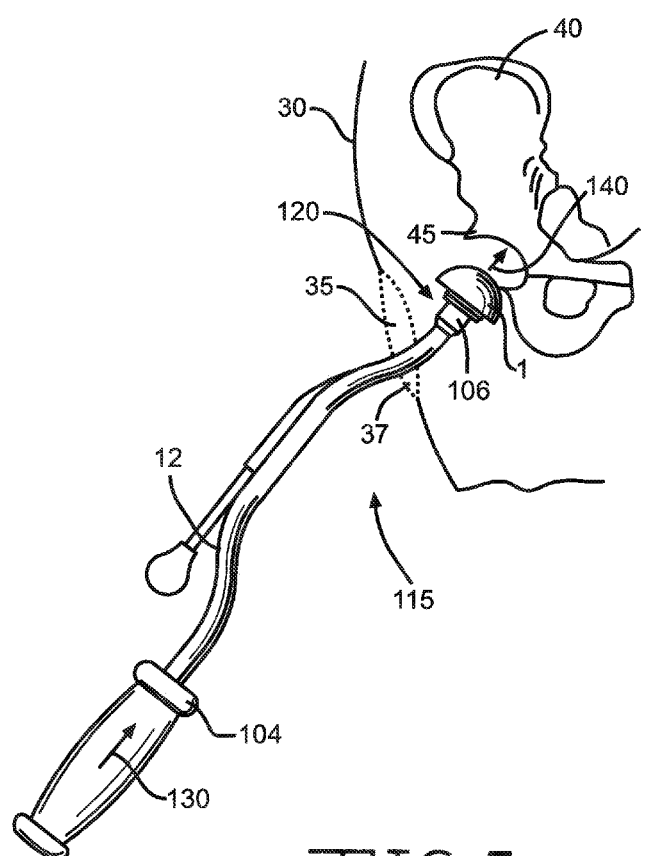
FIG. 5 is a schematic view of the inserter of the present invention in operation.

Referring to FIGS. 4-5, a prior art inserter 15 and the present invention inserter 115, respectively, are shown passing through a miniature incision 35 in the patient's skin 30. In FIG. 4, the inserter 15 is shown approaching the acetabulum 40 in an orientation desirable to ream the socket 45. The difficulty with the prior art spindle 15 is shown as the shaft 3 impinges on the miniature incision 35 at edge of the incision 37. The current surgical protocols are being pushed to the limits and the incision sizes are being reduced in the hopes of increasing the patient's speed to recovery. In some cases surgeons are using a two-incision approach, one to reach the acetabulum and the other to reach the femur. Either one incision or two incision techniques demand less trauma to the patient requiring the instruments to be more optimally designed to make up for the lack of operating space. The reamer of FIG. 5 shows the present invention inserter 115, which has a bent housing 12 containing the drive shaft 14 (FIG. 1A).

It is important to place the bends in the housing at critical locations to pass through the miniature incision without impinging on the skin 30 at 37 while still maintaining the same surgical protocol. The reason why the drive end 104 and the holding mechanism 120 need to be in line or on parallel axis is so that the applied force 130 results in an axial motion 140. This allows the surgeon to maintain the existing technique since inherently the prior art inserter 15 in FIG. 4 would give the same result since it has a straight drive shaft 3. This allows the surgeon to apply a load directly along the path of reaming.

It should be noted that a second head (not shown) can be mounted onto the front of the device 10, the head formed so as to conform with a surface of an acetabular cup liner, in order to enable the device to seat a liner as well as the cup.

The attached drawings represent, by way of example, different embodiments of the subject of the invention.

Referring now to FIGS. 6A, 6B, 6C, 6C', 6D and 6D', an alternate embodiment of the inserter 10' is shown having a safety release 50' having a pin 50'a connected to a base plate 50'b, and spaced apart and parallel with the pin, a second spring pin 51 having a boss 50'd which retains a spring 51, acting between the boss and a surface 12a of the housing 12. Such an arrangement biases the pin 50'a upward in a position which holds the cross pin 46 of the drive train 14 into place. When the prosthetic cup 11 is not fully seated and the surgeon impacts it by mistake, pins that hold the mechanism together are highly stressed. Therefore, a means to enable the mechanism to break free without damage provides a significant advantage. The pin 50'a has a rounded head so as to facilitate removal of the cross pins 46 from their respective divots 44' without damage thereto and thus allowing disassembly of the inserter 10'. Further, the retention force of the safety release 50' is selected so as to release the cross pins 46 from the divots 44'when the torsion or the stresses on the drive train 14 (for example, from use of the inserter as an impactor) reach a threshold amount. Such stresses typically occur when there is no tension on the drive train 14 and the cross pins 46' collide with the safety pin 50'a. Using this embodiment, it is also possible to release the cross pin 46' from the divot 44' by the operator pulling down on a portion of the plate 50'b that extends beyond the side wall of the housing 12.

Referring now to FIGS. 6C and 6D, release of the cross pins 46 from the divots 44' is shown.

Figure 7:
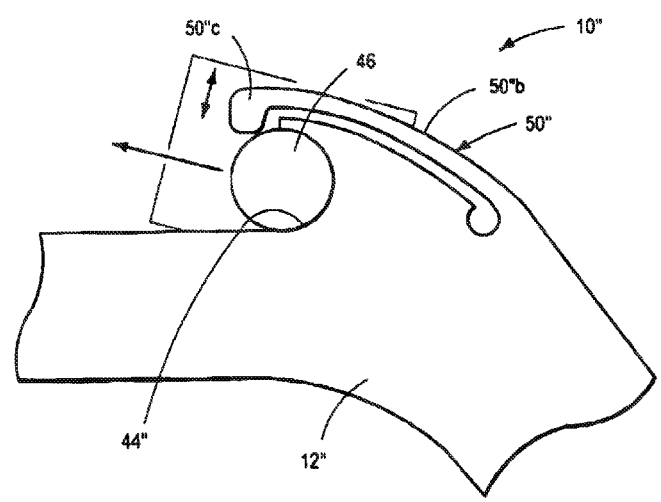
FIG. 7 is a side view of an alternate embodiment of the drive train locking device of the invention.

Referring now to FIG. 7, a second alternate embodiment of the inserter 10" substitutes the safety release 50' with an integrated safety release 50" made up of a flexible finger 50"b extending from the housing (and integral therewith), over the cross pin 46, and retaining the cross pin by means of a blocking head 50"c. The flexible finger is preferably cut using a wire-cut EDM device, but may also be formed in a large variety of ways, including by attachment of a separate spring finger (i.e., is not integral with the housing).

It should be noted that a second head (not shown) can be mounted onto the front of the device 10, the head formed so as to conform with a surface of an acetabular cup liner, in order to enable the device to seat a liner as well as the cup.

Figure 8:
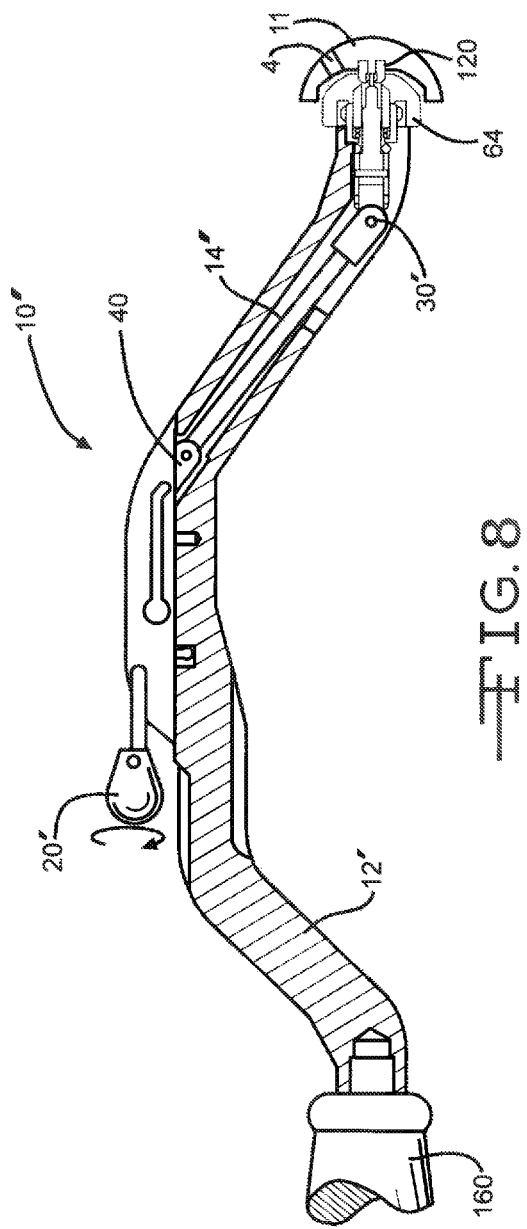
FIG. 8 is a side, cross sectional view of an alternate embodiment of the inserter of the invention.

Referring now to FIG. 8, in another embodiment, an acetabular inserter 10' is provided to aid the surgeon in controlling the installation of a hip prosthesis 11. The inserter 10' has a housing 12' which encloses a drive train 14' having, at a far end, a prosthesis engaging expandable collet mechanism 120 and at the opposite end, a knob or handle 20' which facilitates turning of the drive train by the operator. The housing 12' may be C-shaped, as shown, in order to minimize the invasiveness of the surgery by better clearing anatomical structures and tissue.

When the drive train 14' is drawn inwardly by squeezing the lever 42 towards the housing 12', the prosthesis-engaging expandable collet device 120 locks the prosthesis 11 against the collet mechanism 120. This mechanism enables the surgeon to pre-set and lock the position of the prosthesis 11 prior to the installation thereof. Such selective locking of the prosthesis 11 is important because the prosthesis 11 often has pre-drilled holes 4 and thus, these must be properly positioned prior to fastening through these holes. It should be noted, however, that the expandable collet mechanism 120 is not limited to prosthesis 11 with pre-drilled holes 4, such an embodiment with the expandable collet 120 could also be used with what are referred to as double mobility prosthetic implants which do not have pre-drilled holes 4. The expandable collet device 120 eliminates the need of threading the acetabular prosthesis 11 onto the end of the inserter 10' as the prosthesis can simply be placed over the expandable collet 126' (FIG. 10) and the expandable collet expanded so as to grip the internal surface of the prosthesis 11. Note that to improve the likelihood of proper alignment, the lip 128 on the fingers 127 may be replaced with longitudinally aligned dimples (not shown) having a profile that resembles threads or tubes but yet which minimizes the need for precise orientation of the internal threads of the prosthesis and the dimples on the fingers 127 of the expandable collet device 120.

In operation, the prosthesis 11 first is placed over or threaded onto the expandable collet mechanism 120 via a threaded or undercut hole (not shown). In a second step, the prosthesis 11 is oriented with respect to the form of the inserter 10', in order to minimally impact soft tissue. In a third step, the handle 160 of the inserter 10' is gripped and the prosthesis 11 placed through the incision 35. In a fourth step, the inserter 10' is used to impact the prosthesis 11 in place by impacting a rear portion of the inserter with a mallet, for example. In a fifth step, the knob 20' is turned in an opposite direction in order to release the prosthesis 11. In a final step, the inserter 10' is removed from the incision 35.

Figure 10:
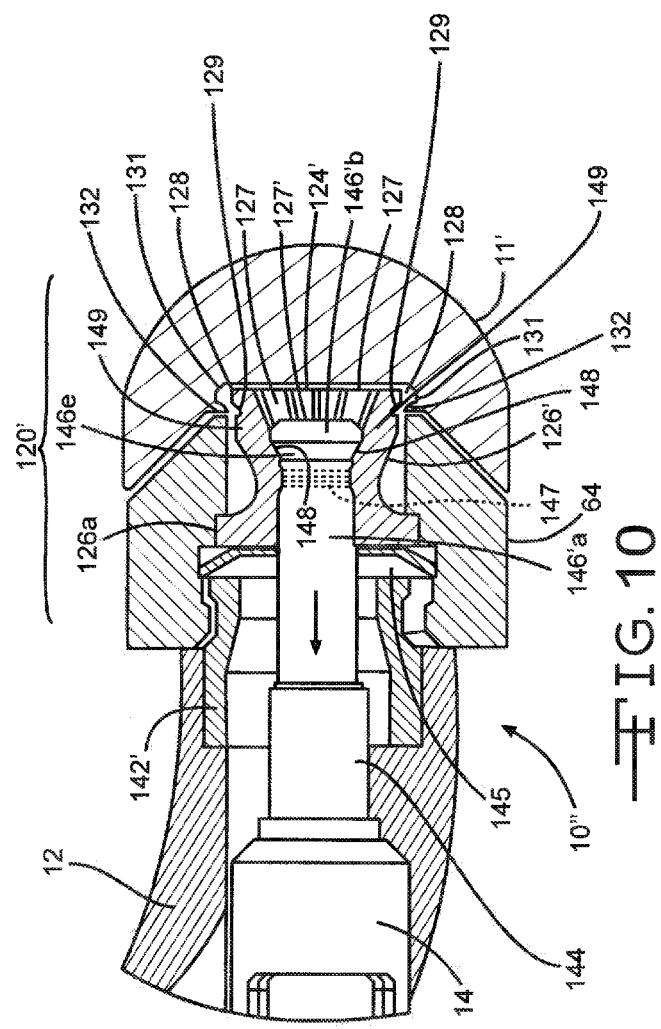
FIG. 10 is a side, cross-sectional view of the collet mechanism of the present invention.

Optionally, with the current design, it is envisioned that the prosthesis 11 can be inserted into the incision 35 as a first step. This optional procedure is used to take advantage of being able to more freely maneuver the prosthesis 11 into the incision and roughly position it prior to inserting the expandable collet device 120 of the inserter 10' into a mating hole. The lever 46 may then be pressed towards the housing 12, thereby drawing the plunger 146'a (FIG. 10) proximally from the fingers 127 (FIG. 10). This actuates opening of the expandable collet mechanism 120 and thus the fixing of the prosthesis 11 on the end of the inserter 10'. These optional steps substitute for the above mentioned four steps.

The "easily cleaned" objective of the invention 10, 10', 10" enables access to all surfaces as that they can be cleaned (parts covering another part can be moved or removed to expose all surfaces), the reduction in number of small radius internal corners, crevices and small gaps and the absence of blind holes.

Figure 9:
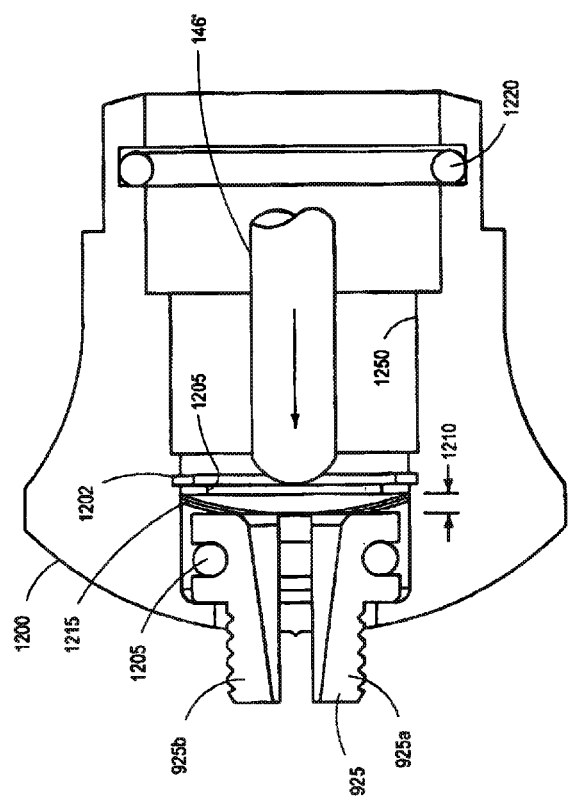
FIG. 9 is a side, cross-sectional view of an inserter head of the prior art.
Figure 11A:
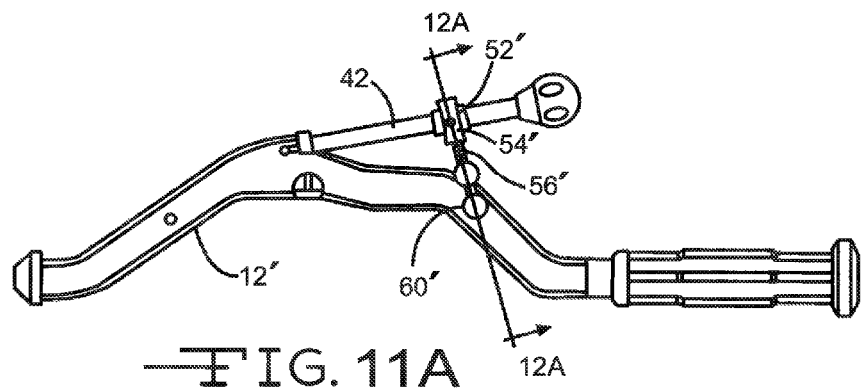
FIG. 11A is a side view of an alternate embodiment of the invention.
Figure 12A:
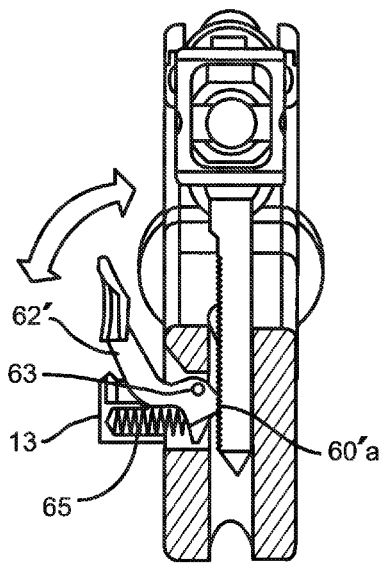
FIG. 12A is a sectional view taken along line 12A-12A of FIG. 11A showing the mechanism in a locked position.
Figure 12A:
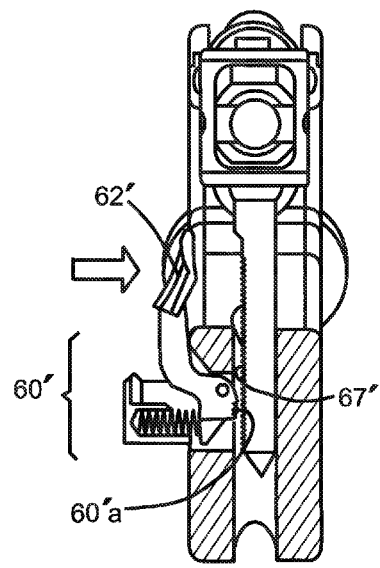
Figure 11B:
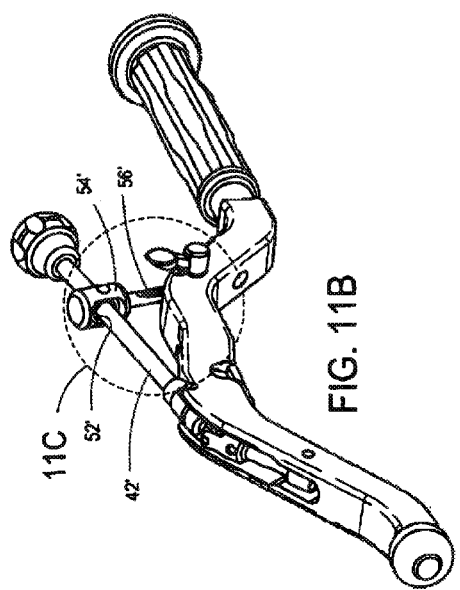
FIG. 11B is a perspective view of the alternate embodiment of the invention.
Figure 11C:
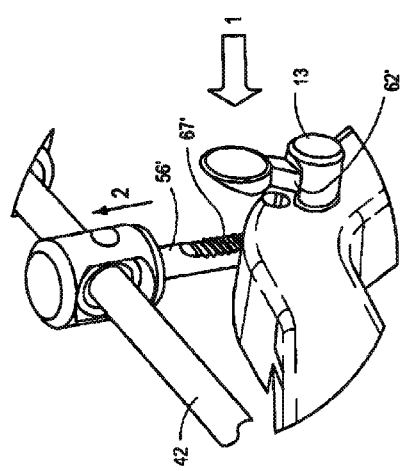
FIG. 11C is a close up view of a portion 11C of the embodiment shown in FIG. 11B.

Referring now to FIG. 9, a cross section of FIG. 12 of a prior art patent application publication No. 20050038443 (the '443 publication), expandable jaws 925 of the prior art are shown. The following is a description essentially copied from the '443 publication:

Jaws 925 extend out through the face 1200 of cup attachment 920 and are held in place by a retaining ring 1202, a washer 1205, and a spring 1215 (spring 1215 is a Belleville washer in one embodiment). An O-ring 1220 urges jaws 925 against actuator 1000 (FIG. 10 of the '443 publication) so that jaws 925 close as actuator 1000 is withdrawn. Spring 1215 forces jaws 925 out through face 1200 of cup attachment 920. A gap 1210 between jaws 925 and washer 1205 prevents jaws 925 from taking the force of hammer blows by allowing jaws 925 to recede into cup attachment 920 until face 1200 engages the interior surface of cup 200. Face 1200, and not the more fragile jaws 925 and associated drive mechanism, thus absorbs the impact. A second O-ring 1220 prevents blood and debris from entering cup attachment 920 between attachment 920 and conduit 905. Though not shown here, attachment 920 includes female threads on an inside surface 1250 that mate with threads 1100 on the outside of conduit 905 (FIG. 11 of the '443 publication). Further, in the prior art device shown, a plunger 146' moves outwardly, into a position between the opposing jaws 925a and 925b, to urge the jaws against opposing surfaces of the implant 11. As with the embodiment already described, this prior art version grips essentially at two opposing points on the internal threaded surface of the implant 11. Further, unlike the embodiment just described, the action of the plunger 146' (FIG. 9) does not concurrently help secure the implant 11 against rotation because it does not concurrently draw the implant against the face 1200 of the head of the prior art device.

Referring now to FIG. 10, an improved embodiment 10" substitutes a single collet 126 for jaws 925 of the prior art. The collet 126' includes a set of fingers 127 having a bulbous, annular lip 128 which extends around the circumference of the collet 126'. In one embodiment there are three fingers. The collet 126' is fixed in position via a keyway in the impactor head 64 and held in place by a Bellville spring 145 interposed between the collet 126' and a threaded collar 142'. The Belleville spring 145 biases between the collet 126' and the impactor head 64. A collet tab 126a keeps the collet 126' from rotating. The Bellville spring 145 abuts against a face 126b of the collet 126' and provides a backstop of the proximal longitudinal movement of the collar 126'. The collet 126', however, is not completely fixed into position, the resistance of the Bellville spring 145 allows for limited longitudinal movement of the collet 126'.

A plunger 146'*a* is placed longitudinally inside the collet mechanism 120'. The proximal end of the plunger 146'*a* is connected to the drive rod 144. An enlarged head 146'*b* is formed at or threaded 147 to the distal end of the plunger 146*a*'. A tapered surface 146*e* extends radially and outwardly from the distal end of the plunger 146'*a*, and gradually transitions into the enlarged head 146'*b*. The shaft of the plunger 146'*a* is placed through a central opening of the Bellville spring 145 which abuts the proximal end of the collet 126'. The collet 126' has a longitudinal bore 126C that receives the distal portion of the plunger 146'*a* and envelopes the enlarged head 146'*b*. The distal end of the enlarged head 146'*b*, contacts the interior surface 127' of the fingers 127 of the collet 126'. The collet 126' is comprised of at least three fingers 127. The collet fingers 127 are provided with external, elongate tubular structures, which are contactable with the interior surface of a prosthesis cup.

The plunger 146'*a* is connected to the drive train 14 via the drive rod 144 so as to be drawn into the housing 12 when the lever 42 is depressed towards the housing. The initial drawing of the plunger 146'*a* into the housing 12 first causes the tapered surface 146*e* of the enlarged head 146*b*' to contact the internal collet surface 148 as the tab 126*a* of the collet 126' interfaces with a recess (not shown) in the housing 12. Since the proximal motion of the collet 126' is impeded by the resistance of the Bellville spring 145, the ramming motion of the enlarged head 146'*b* against the smaller diameter internal collet surface opening 148, forces the surrounding internal collet region 149 to expand.

Further proximal motion of the tapered surface 146*e* of the enlarged head 146*b*' ramming against internal collet surface 148 further causes the internal collet region 149 and annular collet lips 128 to expand outwardly. The outward motion of the collet 126' forces the finger distal ends 124' and the collet annular lips 128 to press against the internal surfaces of the prosthetic cup 11'.

The proximal motion of the plunger 146'*a* causes the bulbous fingers 127 of the collet to first move away from each other, expanding the distal diameter of the collet 126' and increasing the surface area of the distal end of the collet 126' and contacting the internal surface of the prosthetic cup 11'. The collet 126' and bulbous fingers 127 are made from pliable polymeric materials which permit their expansion.

When plunger 146'*a* is drawn proximally by the drive rod 144, the tapered surface 146*e* of the enlarged head 146'*b* rams against the internal collet surface 148. The ramming motion expands the internal collet region 149 outwardly which in turn separates and expands bulbous fingers 127. As collet 126' expands, the annular collet lips 128 seat into annular prosthetic cup groove 128. In a similar fashion, the annular prosthetic cup rim 132 mates with annular collet groove 129 as it expands and meets the prosthetic cup rim 132. These two mating engagements occur at about the same time.

The expanding bulbous fingers 127 create an additional interference fit between the distal collet surface 124' and the internal surface of the prosthetic cup 11'. As a result of the multiple engagements between the collet 126' and prosthetic cup 11', a substantially frictionally tight engagement is created therebetween. These engagements, as previously mentioned, include the mating of the bulbous fingers 127 to the interior surface of the prosthetic cup 11' and, in particular, the mating of the corresponding annular collet lip 128 to the prosthetic cup annular groove or recess 131, and the mating of the prosthetic cup annular rim or ledge 132 to that of the annular collet groove or recess 129. Once the prosthetic cup 11' becomes firmly locked to the collet mechanism 120', the cup 11' is ready for insertion in the acetabulum. This enables the surgeon to accurately and securely manipulate the prosthesis 11' into final position.

In an advantage, the multiple fingers 127 of the collet 126' of FIG. 10 more evenly distribute the forces to the prosthesis 11, thus avoiding damage to the surfaces thereof which the fingers contact. Further, such multi-point contact allows for more firm fixing of the prosthesis 11 for more accurate and precise placing of the prosthesis in the acetabulum, as compared to jawed type devices of the prior art.

Referring now to FIGS. 11A-11C, 12A and 12B, an alternate embodiment of the locking device of FIG. 1C includes a slideable sleeve 52' which is slid over the lever 42 and has a trunnion 54' to which a rod 56' is pivotally attached. The rod 56 has a rack 67' and passes through a one-way catch 60' in the housing 12'. The one-way catch 60' has an inner recess that matches the outer diameter of the rod 56'. The one-way catch 60' is a pawl 62' which pivots on a pin 63 fixed to the housing 12' such that the pawl pivots on an axis which is substantially perpendicular to the axis of the rod 56'. The catch 60' is biased by a spring 65 in a spring housing 13 so that teeth 60*a*' of the catch engage the teeth 67' of the rod 56' to ensure that the rod locks progressively as the lever 42 is pressed toward the housing 12'. The rod 56' is held firmly in place, even during heavy impacting, unless an unlock lever 62*b*' is pressed to permit the rod to back out of the housing 12. Any number of alternative one-way lock devices may be used, the selection of which being within the skill of a person of ordinary skill in this field.

The inner recess has a ratchet pawl (not shown) that locks against one way ratchet teeth 67. This allows the rod 56 to slide into the housing 12, but prevents the rod from sliding out of the housing unless an unlock lever 68 is activated, such lever merely rotating the teeth 60*a*' of the pawl away from the teeth 67' of the rod (as shown in FIG. 12B) to permit the rod to back out of the housing. The placement of the pin 63 of the pawl 62' so that it is perpendicularly located with respect to the axis of the rod 56 is important because in this position, shock during heavy impaction tends to tighten the locking relationship between the teeth 67' of the rod 56' and the teeth 60*a*' of the pawl 62' (see in particular, FIG. 12A).

In another advantage, the locking action in which the plunger 146*a*' is drawn into the housing 12, concurrently pulls the prosthesis 11 into engagement against the face 141*a* of the inserter head 141, thus further securing the prosthesis 11 and providing significantly better handling thereof.

Figure 13:
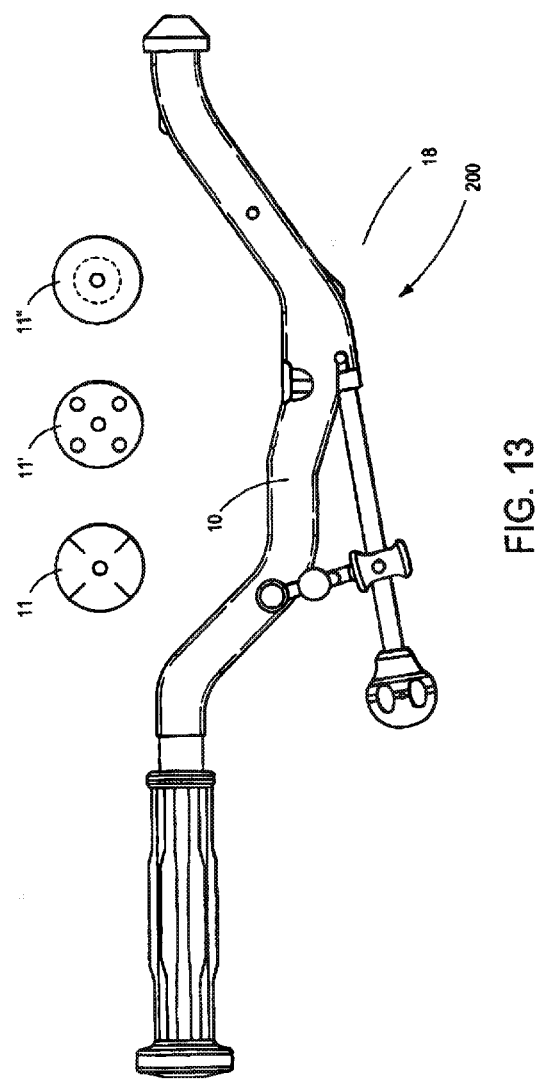
FIG. 13 is a top view of a kit of the invention.

Referring now to FIG. 13, a kit 200 is shown that includes the inserter 10, a variety of prosthetic implants 11, 11', and 11". A case (not shown) conveniently holds the components of the kit in place so as to be readily available when needed.

In an advantage, the inserter 10' is simple and easy to use, without complex and possibly confusing locks activated with the thumb.

In another advantage, it is simple to select a desired orientation of the prosthesis 11.

In another advantage, due to the drawing of the prosthesis 11 against the impaction head 40, the connection between the prosthesis 11 is robust as the connection is made without any play or gaps therebetween, ensuring good support during impaction.

An objective is to provide an inserter 10, 10', 10" that is easy to disassemble and for which the disassembly is easy to learn.

Another object of the invention is to provide a dual mechanism that uses common components to lock the implant in place as well as to provide for easy disassembly for cleaning and sterilization.

Another object of the invention is to minimize the number of pieces and the risk that parts could be lost.

The object of the invention is to provide an inserter 10, 10', 10" which enables the implant to be locked in an annular orientation prior to installation of the implant.

The attached drawings represent, by way of example, different embodiments of the subject of the invention. Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An inserter for aiding a surgeon in controlling the installation of a prosthesis cup, the inserter comprising:
    a) a housing comprising a proximal housing end and a distal housing end supporting an impactor head;
    b) a drive train at least partially housed inside the housing, the drive train comprising:
        i) a first lever comprising a first lever proximal end spaced apart from a first lever distal end located adjacent to the distal housing end;
        ii) a first sleeve pivotably connected to the housing, wherein the first lever is in a slidable relationship with a first opening in the first sleeve disposed at an intermediate location between the first lever proximal end and the first lever distal end;
        iii) a second lever comprising a second lever proximal end located adjacent to the proximal housing end and spaced apart from a second lever distal end, wherein the second lever is pivotably supported by the housing;
        iv) a drive rod comprising a drive rod proximal end space apart from a drive rod distal end that is configured to be connectable to a prosthesis cup,
        v) a plunger comprising a plunger proximal region and a plunger distal region;
        vi) a collet comprising a collet proximal region and a collet distal region surrounding at least the plunger distal region;
        vii) a Bellville spring biasing the collet in a distal direction, the Belleville spring comprising an opening through which the plunger extends;
        viii) wherein the second lever distal end is in a universal joint relationship with the first lever proximal end, the first lever distal end is in a universal joint relationship with the drive rod proximal end, and the drive rod distal end is connected to the plunger proximal region; and
    c) wherein the second lever proximal end is manipulable from a first lever position spaced from the housing to a second lever position spaced closer to the housing than the first lever position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the plunger having an enlarged head, to move proximally, from a first plunger position spaced from the housing to a second plunger position that is closer to the housing than the first plunger position, and to thereby cause the enlarged plunger head to ram against an internal collet surface of a diameter less than that of the enlarged head to thereby cause the collet to move against the bias of the Belleville spring as the collet expands from a first configuration to a second configuration having a larger cross-section than the first configuration.

2. The inserter of claim 1 wherein the collet mechanism is comprised of at least three fingers, each having a distal, prosthesis-engaging end which are adapted to contact an interior surface of a prosthesis cup as the enlarged head of the plunger rams against the internal collet surface, expanding the collet into the second configuration as the prosthesis-engaging ends move away from one another.

3. The inserter of claim 2 wherein the fingers of the collet are provided with external, elongate tubular structures, which are contactable with the interior surface of a prosthesis cup.

4. The inserter of claim 2 wherein at least the collet fingers are comprised of a polymeric material.

5. The inserter of claim 1 wherein the distal region of the collet has an annular collet lip which is seatable into an annular cup groove of a prosthesis cup creating a substantially friction tight engagement therebetween.

6. The inserter of claim 1 wherein the distal region of the collet has an annular collet groove that is matable with an annular cup rim of a prosthesis cup creating a substantially friction tight engagement therebetween.

7. The inserter of claim 1 wherein an annular collet lip and an annular collet groove of the collet together are matable with a corresponding annular cup groove and annular cup rim of a prosthesis cup for creating a substantially friction tight engagement therebetween.

8. The inserter of claim 1 wherein the proximal region of the collet has a tab portion that interfaces with a recess in the impactor head.

9. The inserter of claim 1 wherein the Bellville spring biases between the collet proximal region and the impactor head.

10. The inserter of claim 1 wherein the enlarged plunger head is threaded to the distal end of the plunger.

11. The inserter of claim 1 wherein the collet is made of a polymeric material.

12. A surgical kit for minimally invasive surgery, the kit including:
    a) a case having recesses into which components of the kit may be conveniently stored until use;
    b) at least one orthopaedic implant; and
    c) an inserter according to claim 1 for aiding a surgeon in controlling installation of the orthopedic implant.

13. The surgical kit of claim 12 wherein the inserter further comprises:
    a) a first rod comprising a first rod proximal end pivotably connected to the second sleeve and a first rod distal end adjustably connected to the housing in a one-way catch relationship; and
    b) wherein when the second lever proximal end is manipulated from the first lever position spaced from the housing to the second lever position spaced closer to the housing than the first lever position, that movement adjusts the one-way catch relationship between the first rod distal end and the housing as the second lever pivots with respect to the first rod proximal end and moves along the second opening in the second sleeve and as the second lever pivots on the housing, to thereby lock the drive rod in the drive rod second position with respect to the plunger.

14. The surgical kit of claim 12 wherein the orthopeadic implant is a prosthetic cup.

15. An inserter for aiding a surgeon in controlling the installation of a prosthesis cup, the inserter comprising:
 a) a housing comprising a proximal housing end and a distal housing end supporting an impactor head;
 b) a drive train at least partially housed inside the housing, the drive train comprising:
  i) a first lever comprising a first lever proximal end spaced apart from a first lever distal end located adjacent to the distal housing end;
  ii) a first sleeve pivotably connected to the housing, wherein the first lever is in a slidable relationship with a first opening in the first sleeve disposed at an intermediate location between the first lever proximal end and the first lever distal end;
  iii) a second lever comprising a second lever proximal end located adjacent to the proximal housing end and spaced apart from a second lever distal end, wherein the second lever is pivotably supported by the housing;
  iv) a drive rod comprising a drive rod proximal end space apart from a drive rod distal end that is configured to be connectable to a prosthesis cup,
  v) a plunger comprising a plunger proximal region and a plunger distal region;
  vi) a collet comprising a collet proximal region and a collet distal region surrounding at least the plunger distal region;
  vii) a Bellville spring biasing between the collet proximal region and the housing to thereby bias the collet in a distal direction, the Belleville spring comprising an opening through which the plunger extends;
  viii) wherein the second lever distal end is in a universal joint relationship with the first lever proximal end, the first lever distal end is in a universal joint relationship with the drive rod proximal end, and the drive rod distal end is connected to the plunger proximal region; and
 c) wherein the second lever proximal end is manipulable from a first lever position spaced from the housing to a second lever position spaced closer to the housing than the first lever position to cause the second lever to pivot with respect to the housing and thereby move the second lever distal end away from the distal housing end and to further cause the first lever to move away from the distal housing end along the first opening in the first sleeve as the first sleeve pivots on the housing to thereby cause the plunger having an enlarged head, to move proximally, from a first plunger position spaced from the housing to a second plunger position that is closer to the housing than the first plunger position, and to thereby cause the enlarged plunger head to ram against an internal collet surface of a diameter less than that of the enlarged head to thereby cause the collet to move against the bias of the Belleville spring as the collet expands from a first configuration to a second configuration having a larger cross-section than the first configuration.

16. The inserter of claim 15 wherein the collet mechanism is comprised of at least three fingers, each having a distal, prosthesis-engaging end which are adapted to contact an interior surface of a prosthesis cup as the enlarged head of the plunger rams against the internal collet surface, expanding the collet into the second configuration as the prosthesis-engaging ends move away from one another.

17. The inserter of claim 15 wherein with the collet in the second configuration, a first annular lip and a second annular groove of the collet are matable to a corresponding first annular groove and a second annular rim of a prosthesis cup for creating a substantially friction tight engagement therebetween.

18. The inserter of claim 15 wherein the Bellville spring biases between the collet proximal region and the impactor head.

19. An inserter for aiding a surgeon in controlling the installation of a prosthesis cup, the inserter comprising:
 a) a housing comprising a proximal housing end and a distal housing end supporting an impactor head;
 b) a drive train at least partially housed inside the housing;
 c) a plunger comprising a plunger proximal region and a plunger distal region, wherein a distal end of the drive train is connected to the plunger proximal region;
 d) a collet comprising a collet proximal region and a collet distal region surrounding at least the plunger distal region; and
 e) a Belleville spring biasing the collet in a distal direction and comprising an opening through which the plunger extends,
 f) wherein a proximal end of the drive train is manipulable from a first position spaced from the housing to a second position spaced closer to the housing than the first position to thereby cause the plunger having an enlarged head, to move proximally, from a first plunger position spaced from the housing to a second plunger position that is closer to the housing than the first plunger position, and to thereby cause the enlarged plunger head to ram against an internal collet surface of a diameter less than that of the enlarged head to thereby cause the collet to move against the bias of the Bellville spring as the collet expands from a first configuration to a second configuration having a larger cross-section than the first configuration.

20. The inserter of claim 19 wherein the Bellville spring biases between the collet proximal region and the impactor head.

* * * * *

UNITED STATES PATENT AND TRADEMARK OFFICE
CERTIFICATE OF CORRECTION

| | | |
|---|---|---|
| PATENT NO. | : 8,277,457 B1 | Page 1 of 1 |
| APPLICATION NO. | : 12/724505 | |
| DATED | : October 2, 2012 | |
| INVENTOR(S) | : Burgi et al. | |

It is certified that error appears in the above-identified patent and that said Letters Patent is hereby corrected as shown below:

In the Specifications

Column 2, line 37 insert:
    --FIG. 6C' is an enlarged view of FIG. 6C, partly in phantom, showing the cross pin 46 of the drive train 14 seated in a divot 44' of the housing 12.
    FIG. 6D' is a dissassembled view of FIG. 6D, partly in phantom and partly broken away, showing a spring 51 biased pin 50'c acting between a boss 50'd and a surface 12a of the housing 12 to bias a pin 50'a upwardly to thereby hold the cross pin 46 of the drive train 14 against a divot 44'.--

Column 5, line 1 insert a space after "44'."

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,277,457 B1  
APPLICATION NO. : 12/724505  
DATED : October 2, 2012  
INVENTOR(S) : Burgi et al.

Page 1 of 1

It is certified that error appears in the above-identified patent and that said Letters Patent is hereby corrected as shown below:

In the Specification

Column 4, line 55 delete "51" and insert --50'c--

Signed and Sealed this
Twenty-third Day of September, 2014

Michelle K. Lee
*Deputy Director of the United States Patent and Trademark Office*